United States Patent
Famodu et al.

(10) Patent No.: US 6,294,658 B1
(45) Date of Patent: Sep. 25, 2001

(54) FACTORS INVOLVED IN GENE EXPRESSION

(75) Inventors: Layo O. Famodu, Newark, DE (US); Joan T. Odell, Unionville, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/347,833

(22) Filed: Jul. 2, 1999

Related U.S. Application Data

(60) Provisional application No. 60/092,415, filed on Jul. 10, 1998.

(51) Int. Cl.$^7$ .............................. C07H 15/11; C07H 15/18
(52) U.S. Cl. ................. 536/23.1; 536/23.1; 536/23.6; 435/320.1; 435/252.3; 435/419; 435/254.2
(58) Field of Search ................ 536/23.1; 435/320.1, 435/252.3, 419, 254.2

(56) References Cited

PUBLICATIONS

GenEmbl Accession No. P93616. Le et al. Poly (A) binding protein, May 1, 1997.*
Watson et al. Recombinant DNA, 2nd Edition. pp. 453–455, 1992.*
Vries et al., (1997) J. Biol. Chem., 272:32779–32784.
Yam et al., (1992) J. Biol. Chem. 267:23226–23231.
Craig et al., (1998), Nature 392:520–523.
Burd et al., (1991) Mol. Cell biol. 11:3419–3424.
Mol. Cell Biol. 17(12), 6940–6947 (1997) Imataka and Sonenberg.
J. Biol. Chem. 268(26), 19200–19203, (1993) Lamphear et al.

* cited by examiner

Primary Examiner—Karen Cochrane Carlson
Assistant Examiner—Patricia Robinson

(57) ABSTRACT

This invention relates to an isolated nucleic acid fragment encoding a factor involved in gene expression. The invention also relates to the construction of a chimeric gene encoding all or a portion of the factor involved in gene expression, in sense or antisense orientation, wherein expression of the chimeric gene results in production of altered levels of the factor involved in gene expression in a transformed host cell.

9 Claims, 3 Drawing Sheets

```
SEQ ID NO:11   MAAAAASSASGGSAAAAAAAAAAASSATS------------YVGD-DVSV-DADV------AGGV
SEQ ID NO:02   MSAQVAVVPNGGPGAVPAVVSPGAVGVAQPLPTTSLYVGDLEGAVSDSQLYKLFSQAGQV
SEQ ID NO:04   QAVPAAEGGGAPPQANGVVAAGSAAAAAAATFQATSLYVGDLDVSVQDAQLFDVFSQVGSV
SEQ ID NO:06   ------------------------------------------------------------
                1                                                          60

SEQ ID NO:11   VSVRVCRDVTSRKS-GYAYVNYNTA-DAARARAMNTNG------------RRMYSNRD--SRKSG
SEQ ID NO:02   VSVRVCKDVTSRRSLGYAYVNYSNPLDAARALEVLNFAALNNKPIRVMYSNRDPSSRRSG
SEQ ID NO:04   VSVRVCRDVNTRLSLGYAYVNFSSPADAARALEMLNFTPINGKPIRIMYSNRDPSSRKSG
SEQ ID NO:06   ------------------------------------------------------------
                61                                                        120

SEQ ID NO:11   TANKNDKSDNKAYD---------TCVGN--SCKVATDAG--SKGYGVYR-DAAHAAKNG--
SEQ ID NO:02   SANIFIKNLDKTIDNKTLHETFSSFGTILSCKVAVDEAGQSKGFGFVQYDKEEAAQNAIK
SEQ ID NO:04   AANIFIKNLDKSIDNKALYDTFSVFGNILSCKVATEMSGESKGYGFVQFELEEAAQNAIS
SEQ ID NO:06   ------------------------------------------------------------
                121                                                *      180

SEQ ID NO:11   -----MMNDKKVYVG--VRKRDNS---GNVK-NNVYVKNATTDDKGK-------GAT
SEQ ID NO:02   SLNGMLINDKPVFVGPFVRKQERDHSFDKTKFNNVFVKNLSESTTKEDLLKIFGEYGDIT
SEQ ID NO:04   KLNGMLLNDKKVYVGPFVRKQERENVSGNPKFNNVYVKNLSESTTEDNLKEIFGKFGPIT
SEQ ID NO:06   ----------------------------------------DEELMKFFGEYGTIT
                181                                                       240
```

FIG. 1-1

```
                   *  *   **  ****        ****              ***   *  ***
SEQ ID NO:11   SVVVMRDGDGRSKC------GVNSDAAAVD--NGKKSDK--WYVGRA-KKSRKKKNAAD
SEQ ID NO:02   SAVVMIGMDGKSRCFGFINFENPDAASHAVQELNGKKINDKEWYVGRAQKKSEREMELKR
SEQ ID NO:04   SVVVMREGDGKSRCFGFVNFENPDDAARAVEDLNGKKFDDKEWYVCRAQKKSEREMELKE
SEQ ID NO:06   SAVIMRDADGKSRCFGFVNFENPDDAAKAVEGLNGKKVDDKEWYVGKAQKKSEREQELKG
                241                                                     300

*                      **  ******  *   ***
SEQ ID NO:11   KYNTNYKN-----------DDTVDDKR------------------AGTTSCKVMRDSNGASRGSG
SEQ ID NO:02   RFEQSLKDAADKYQGLNLYLKNLDDSIGDDQ-LCELFSNFGKITSYKVMRDQNGLSKGSG
SEQ ID NO:04   KFEKNIKEAADKNQGTNLYLKNLDDSIDDDEKLKEIFADFGTITSCKVMRDLNGVSKGSG
SEQ ID NO:06   RFEQSIKESADKYQGVNLYLKNLDDTISD-EKLKEMFAEYGTITSCKVMRDPTGIGRGSG
                301                                                     360

**   **  **                   ***         *
SEQ ID NO:11   VA--KSADDASRA--AMNNKMVGNK--YVAA---RKDRKA--------RASMRVMATVG
SEQ ID NO:02   FVAFSTREEASQALTEMNGKMISGKPLYVAFAQRKEDRKAMLQAQFSQMRPAVPMTPTLA
SEQ ID NO:04   FVAFKSAEDASRALVAMNGKMIGSKPLYVALAQRKEERRARLQAQFSQMRP-MVMPPSVA
SEQ ID NO:06   FVAFSTPEEASRALGEMNGKMIAGKPLYVALAQRKEDRRARLQAQFSQMRP-VAITPSVA
                361                                                     420

***
SEQ ID NO:11   RMM-----GVVGM-----YGANGGM----------------GMRGGA-------MNMMMV
SEQ ID NO:02   PRLPMYSPMAP---QQLFYGQAPPAMMPPQPGFAFQQQLVPGMRPGGPHMPNYYVPVVQQ
SEQ ID NO:04   PRMPMYPPGVPGVGQLFYGQPPPAFVNPQPGFGFQQHLIPGMRPSVGPIPNFVMPMVQQ
SEQ ID NO:06   PRMPLYPPGAPGLGQQFLYGQGPPAMMPPQAGFGYQQQLVPGMRPGGGPMPSFFVPMVQQ
                421                                                     480
```

FIG. 1-2

```
SEQ ID NO:11  GR------AGRRAGAGG------MSMMG----MGRGGGRGYRY-TGRGMD---AMHGVGGV
SEQ ID NO:02  GQQGPRPGIRR---GAGAQGQQPVPPFQQQILPRGRM--YRYPTGRNMPEAPAMPGVAGG
SEQ ID NO:04  GQQPQRPAGRRAGTGGIQQP---MPMGHQQMLPRGSRGGYRYASGRGMPDNA-SRGV-GG
SEQ ID NO:06  GQQGQRPGGRR-GTGPVQQPQQPMPMMQQQMLPRGR--VYRYPPGRNMQDVP-LQGVAGG
                                                                   540

SEQ ID NO:11  M--TSY-MGGM-MRDAG--------SVGAASAANSTRMMGNYV-------DHDAA
SEQ ID NO:02  MIQA-YDMGGFPVRDAALSPAAQIGTLTSALANANPEQQRTILGENLYPLVEQLEPNQAA
SEQ ID NO:04  LVPSPYEMGRMPLSDAGAPPQVPIGALASALANSPPDQQRLMLGESLYPLVDQLEHDQAA
SEQ ID NO:06  MMSVPYDMGGLPIRDAVGQP-MPIQALATALANAPEQQRTMLGEALYPLVDQLEHDAAA
                                                                   600

SEQ ID NO:11  KVTGMM---------DTVHSDAKAKVAAMVRSAHTNSAS--------SNDG
SEQ ID NO:02  KVTGMLLEMDQTEVLHLLESPDALKSKVAEAMDVLRNVAHQQNPNLPTSQLAALSLTEGI
SEQ ID NO:04  KVTGMLLEMDQTEVLHLIESPDALKAKVAEAMEVLRNAQQQQ-ANTPTDQLAALTLSDGV
SEQ ID NO:06  KVTGMLLEMDQPEVLHLIESPDALKAKVAEAMDVLRNVAQQQ-TN-PADQLASLSLNDNL
                                                                   660

SEQ ID NO:11  SS
SEQ ID NO:02  MS
SEQ ID NO:04  VS
SEQ ID NO:06  VS
              661 662
```

FIG. 1-3

SEQUENCE LISTING

<160> NUMBER OF SEQ ID NOS: 11

<210> SEQ ID NO 1
<211> LENGTH: 2508
<212> TYPE: DNA
<213> ORGANISM: Zea mays

<400> SEQUENCE: 1

```
ccacgcgtcc gcgtcccccc gcgtgctctc cgcctgcggc ctctgtatcc cgcaaccaaa      60
aactaccccc aaaaaaagaa gaaaccccca aatcctcgag atctatcagt atcgagcgac     120
ttaccaatcc gattgctagg gtttagtttc gaaaaaatct gaaaaaaaat tctggtcgag     180
gggaggaggc gatgtcggcg caagtggcgg tggtgcctaa tgggggcccg ggcgctgtcc     240
ccgcggtggt gtcgccggga gctgtcggcg tggctcagcc tctcccgacc acgtcgctct     300
acgtgggcga cctggagggg gccgtctcgg actcgcagct gtacgaactc ttcagccagg     360
cggggcaggt ggtgtcggtg cgcgtctgca gggatgtcac ctcgcgccgc tcgctcggat     420
acgcctacgt caactacagc aatcccttgg atgctgcgag agcattggaa gtgctgaact     480
ttgctgctct taacaacaag cctatccggg tgatgtattc aaaccgtgat ccaagcagcc     540
gcaggagtgg atctgctaac attttcataa aaaatcttga caagacaata gacaataaaa     600
cccttcatga gacctttttct tcatttggta ccattctctc gtgtaaggta gctgtggatg     660
aagcaggcca atccaaaggc tttggttttg ttcagtatga caagaagaa gctgcgcaga     720 acgctataaa aagtcttaac gggatgctta taaatgataa gcctgttttt gttggacctt     780
ttgttcgcaa gcaagaaaga gatcattctt ttgacaagac aaaatttaac aatgtctttg     840
tgaaaaattt gtctgagtct accacaaagg aagatttact caaaatcttt ggtgaatatg     900
gggatattac aagtgctgtt gtgatgattg gtatggatgg taaatcaagg tgttttggtt     960
tcatcaattt tgagaatcca gatgcagctt cccatgctgt tcaggaactt aatggtaaga    1020
agataaatga caaagagtgg tatgttggaa gagctcagaa gaagtcagaa agagagatgg    1080
aactaaaaag gagatttgag caaagcttga aagatgctgc tgacaaatat caaggactga    1140
acttatacct caagaacttg gatgatagca ttggagatga tcaactttgt gaattgttct    1200
```

-continued

```
ctaactttgg caaaattact tcgtacaagg tgatgcgtga ccaaaatggt cttagcaaag    1260
gctctggatt tgttgctttc tcaactcgtg aggaagcatc tcaggcttta actgaaatga    1320
atggcaaaat gatatctgga aaaccattgt atgttgcatt tgcacagcgc aaagaagata    1380
gaaaagcgat gttgcaggca cagttttctc agatgcgccc tgctgtacca atgacaccca    1440
ctctagcccc acgccttcca atgtactctc cgatggctcc tcagcaactc ttctatggac    1500
aagcgccacc agctatgatg cccctcagc caggatttgc tttccagcaa cagcttgttc     1560
caggcatgag gcctgggggt cctcatatgc caaactatta tgttccggtt gtccaacagg    1620
gccaacaggg tccacgccca ggtattaggc gtggagctgg agcccagggc cagcaacctg    1680
tgccaccatt tcagcagcag attcttccgc gaggacggat gtaccgttac ccaactggtc    1740
gcaacatgcc tgaagctcca gcgatgccag gggttgctgg aggtatgatt caggcatatg    1800
atatgggagg cttccctgtg agagatgctg ccttatcacc ggccgctcaa attgggactc    1860
tgacttctgc ccttgcaaat gctaatcctg agcagcaaag aacgatactt ggtgaaaacc    1920 tatcccact ggttgagcaa ctggaaccaa accaagctgc aaaggtcact ggaatgcttt     1980
tggagatgga tcagaccgag gtcctccacc tgctcgagtc ccctgatgct ctcaagtcca    2040
aggttgctga ggcgatggat gttctccgca atgtggccca ccagcaaaac ccaaacctcc    2100
cgaccagtca gcttgccgca ttatcactga ccgaaggcat tatgtcctaa cttgaaggcc    2160
ataacaaact atcttcagtt tccaactcag tgcgggtgtt tccagaggtt gtctggcaca    2220
tgacagtatt gttccttcga tactatggtt ggacttgtga atgttgtttc catactggat    2280
gttaggtttt atatgcgccc tacggtgacc tgccgttaag gcaaagaact tatttgcaag    2340
tctgagcact attttggggg gtggggtggg gggtgcgttg ttttttataac tgtctttttt    2400 cccctagttg aagtttttct tactcaattg aatgaacgag ggaacttatt gcatactatc    2460
aaatgttttg tgatatggtg ttgagtaatt atcaacacct tggattttt               2508
```

<210> SEQ ID NO 2
<211> LENGTH: 652
<212> TYPE: PRT
<213> ORGANISM: Zea mays

<400> SEQUENCE: 2

```
Met Ser Ala Gln Val Ala Val Pro Asn Gly Gly Pro Gly Ala Val
 1               5                  10                  15

Pro Ala Val Val Ser Pro Gly Ala Val Gly Val Ala Gln Pro Leu Pro
             20                  25                  30

Thr Thr Ser Leu Tyr Val Gly Asp Leu Glu Gly Ala Val Ser Asp Ser
         35                  40                  45

Gln Leu Tyr Lys Leu Phe Ser Gln Ala Gly Gln Val Val Ser Val Arg
     50                  55                  60

Val Cys Lys Asp Val Thr Ser Arg Arg Ser Leu Gly Tyr Ala Tyr Val
 65                  70                  75                  80

Asn Tyr Ser Asn Pro Leu Asp Ala Arg Ala Leu Glu Val Leu Asn
                 85                  90                  95

Phe Ala Ala Leu Asn Asn Lys Pro Ile Arg Val Met Tyr Ser Asn Arg
            100                 105                 110

Asp Pro Ser Ser Arg Arg Ser Gly Ser Ala Asn Ile Phe Ile Lys Asn
        115                 120                 125

Leu Asp Lys Thr Ile Asp Asn Lys Thr Leu His Glu Thr Phe Ser Ser
    130                 135                 140
```

```
Phe Gly Thr Ile Leu Ser Cys Lys Val Ala Val Asp Glu Ala Gly Gln
145                 150                 155                 160

Ser Lys Gly Phe Gly Phe Val Gln Tyr Asp Lys Glu Glu Ala Ala Gln
                165                 170                 175

Asn Ala Ile Lys Ser Leu Asn Gly Met Leu Ile Asn Asp Lys Pro Val
            180                 185                 190

Phe Val Gly Pro Phe Val Arg Lys Gln Glu Arg Asp His Ser Phe Asp
        195                 200                 205

Lys Thr Lys Phe Asn Asn Val Phe Val Lys Asn Leu Ser Glu Ser Thr
    210                 215                 220

Thr Lys Glu Asp Leu Leu Lys Ile Phe Gly Glu Tyr Gly Asp Ile Thr
225                 230                 235                 240

Ser Ala Val Val Met Ile Gly Met Asp Gly Lys Ser Arg Cys Phe Gly
                245                 250                 255

Phe Ile Asn Phe Glu Asn Pro Asp Ala Ala Ser His Ala Val Gln Glu
                260                 265                 270

Leu Asn Gly Lys Lys Ile Asn Asp Lys Glu Trp Tyr Val Gly Arg Ala
            275                 280                 285

Gln Lys Lys Ser Glu Arg Glu Met Glu Leu Lys Arg Arg Phe Glu Gln
        290                 295                 300

Ser Leu Lys Asp Ala Ala Asp Lys Tyr Gln Gly Leu Asn Leu Tyr Leu
305                 310                 315                 320

Lys Asn Leu Asp Asp Ser Ile Gly Asp Asp Gln Leu Cys Glu Leu Phe
                325                 330                 335

Ser Asn Phe Gly Lys Ile Thr Ser Tyr Lys Val Met Arg Asp Gln Asn
            340                 345                 350

Gly Leu Ser Lys Gly Ser Gly Phe Val Ala Phe Ser Thr Arg Glu Glu
        355                 360                 365

Ala Ser Gln Ala Leu Thr Glu Met Asn Gly Lys Met Ile Ser Gly Lys
    370                 375                 380

Pro Leu Tyr Val Ala Phe Ala Gln Arg Lys Glu Asp Arg Lys Ala Met
385                 390                 395                 400

Leu Gln Ala Gln Phe Ser Gln Met Arg Pro Ala Val Pro Met Thr Pro
                405                 410                 415

Thr Leu Ala Pro Arg Leu Pro Met Tyr Ser Pro Met Ala Pro Gln Gln
            420                 425                 430

Leu Phe Tyr Gly Gln Ala Pro Ala Met Met Pro Gln Pro Gly
        435                 440                 445

Phe Ala Phe Gln Gln Gln Leu Val Pro Gly Met Arg Pro Gly Gly Pro
450                 455                 460

His Met Pro Asn Tyr Tyr Val Pro Val Val Gln Gly Gln Gln Gly
465                 470                 475                 480

Pro Arg Pro Gly Ile Arg Arg Gly Ala Gly Ala Gln Gly Gln Pro
            485                 490                 495

Val Pro Pro Phe Gln Gln Ile Leu Pro Arg Gly Arg Met Tyr Arg
        500                 505                 510

Tyr Pro Thr Gly Arg Asn Met Pro Glu Ala Pro Ala Met Pro Gly Val
    515                 520                 525

Ala Gly Gly Met Ile Gln Ala Tyr Asp Met Gly Gly Phe Pro Val Arg
    530                 535                 540

Asp Ala Ala Leu Ser Pro Ala Ala Gln Ile Gly Thr Leu Thr Ser Ala
545                 550                 555                 560

Leu Ala Asn Ala Asn Pro Glu Gln Gln Arg Thr Ile Leu Gly Glu Asn
```

|                                 |     |     |     |     |     |     |     |     |     |     |
| ------------------------------- | --- | --- | --- | --- | --- | --- | --- | --- | --- | --- |
|                                 | 565 |     |     |     | 570 |     |     |     | 575 |     |
| Leu Tyr Pro Leu Val Glu Gln Leu Glu Pro Asn Gln Ala Ala Lys Val |
|     |     |     | 580 |     |     |     |     | 585 |     |     |     | 590 |     |     |

Thr Gly Met Leu Leu Glu Met Asp Gln Thr Glu Val Leu His Leu Leu
            595                 600                 605

Glu Ser Pro Asp Ala Leu Lys Ser Lys Val Ala Glu Ala Met Asp Val
        610                 615                 620

Leu Arg Asn Val Ala His Gln Gln Asn Pro Asn Leu Pro Thr Ser Gln
625                 630                 635                 640

Leu Ala Ala Leu Ser Leu Thr Glu Gly Ile Met Ser
                645                 650

<210> SEQ ID NO 3
<211> LENGTH: 2318
<212> TYPE: DNA
<213> ORGANISM: Oryza sativa

<400> SEQUENCE: 3

```
gcacgaggcg aaacccttgt cttcctccca acccatctta cccaaaccct aaaaaaccaa         60
aaaaaaaatc cgcaaaatta ccccccgaaaa tcccaaaaaa tatcgccgga accctatcct        120
tcgatcggat ccacctatcc ccctccccgg tgatggcggc gcaggttcag gcggtgccgg        180
cggcggaggg tggtggcgcg ccgccgcagg ccaacgggt cgtggctgcg ggctctgctg         240
ccgccgctgc ggcgaccttc caggcgacgt cgctgtacgt gggggacctc gacgtgagcg        300
tgcaggacgc gcagctgttc gacgtcttca gccaggtcgg atcggtggta cggtgcgcg         360
tttgccggga cgtcaatacc aggctgtcgc tgggttacgc ctatgtcaac ttcagcagtc        420
ccgccgatgc tgcaagggca ttggaaatgc tgaacttcac tcctattaac gggaagccta        480
tcaggataat gtattctaac cgtgaccccca gctcacgtaa agtggagca gcaaacatat        540
ttattaagaa tcttgacaag tcaatagata acaaagctct ctatgacaca ttttctgtat        600
ttgggaatat tctttcgtgt aaagtcgcga cggaaatgtc tggagagtcg aagggatatg        660
gttttgttca gtttgagctg gaagaagctg cccagaatgc tatcagtaag ctcaatggga        720
tgcttttgaa tgacaaaaag gtgtatgtag ggccttttgt tcgtaaacag gagagggaaa        780
atgtatcagg caatcccaaa tttaacaatg tgtatgtaaa gaacctatcg gaatcaacaa        840
ctgaagataa tttaaaggaa atttttggta aatttggacc cataactagt gtcgttgtaa        900
tgcgtgaagg tgatgggaaa tctagatgct ttggatttgt taactttgaa atccagatg         960
atgctgctcg agctgttgaa gatttgaatg gcaagaagtt tgatgacaag gaatggtatg       1020
tttgtagagc acagaagaag tcagagaggg agatggaatt gaaagaaaaa tttgagaaga       1080
acatcaaaga ggcagcagat aagaaccagg gaactaactt gtatttgaaa aacttggatg       1140
atagcatcga tgacgatgag aaattaaaag aaatttttgc tgattttggt actattacct       1200
cttgtaaggt catgagagat ttgaatggtg ttagtaaagg atctggcttt gttgcattta       1260
agtctgctga agatgcttca cgagctcttg tggctatgaa tggtaagatg attggcagta       1320
aacctctcta tgtagcactt gcacaacgca aggaagaaag aagggcaagg cttcaggcac       1380
agttctcaca aatgcgtcct atggtgatgc ctccttcagt tgctcctcgt atgcccatgt       1440
atcccccatgg tgtccctggt gtaggccaac agctgtttta tggccagcca cctccagctt       1500
ttgttaaccc tcagcctgga tttggcttcc agcaacatct cattcctggt atgaggccta       1560
gtgttggacc aattccaaat tttgtcatgc ctatggtcca gcaaggtcaa caaccacaac       1620
```

-continued

```
gtccagctgg aaggcgtgca ggcactggtg gaattcagca accaatgcca atgggccacc      1680
agcaaatgct tccaagggt  agtcgtggtg gttaccgtta tgcttctggt cgtggcatgc      1740
cagacaatgc atcccgtggt gttggaggtt tagtgccatc cccatatgag atgggaagaa      1800
tgcctctcag tgatgctggt gcaccccgc  aggtcccaat ggagcattg  gcctctgcac      1860 tggccaattc accccagat  cagcaaagac tgatgcttgg tgaaagttta tacccgcttg      1920
ttgatcagct ggagcatgat caggcagcga aggtcactgg catgcttttg gagatggacc      1980
agactgaagt tctccatctc attgagtcac ctgatgctct taaggccaag gtcgctgagg      2040
ctatggaagt tctccgtaat gctcagcagc agcaggcaaa taccccaact gatcagctag      2100
ctgctctcac cctgagcgac ggcgtcgttt cttaacttgg ttggcatctt atatctgaga      2160
ctgcaagtga tgtagtatgt acttggtgtg ttttggaact tgaacctgtg gggaagtctg      2220
tctttatctt tgttaaacgg cagttcagtt acttcagcat tgtgtggatc tggatttcag      2280
ttcctatttg tgttttctta aaatattggg attgcaat                              2318
```

<210> SEQ ID NO 4
<211> LENGTH: 655
<212> TYPE: PRT
<213> ORGANISM: Oryza sativa

<400> SEQUENCE: 4

```
Gln Ala Val Pro Ala Glu Gly Gly Gly Ala Pro Pro Gln Ala Asn
 1               5                  10                  15

Gly Val Val Ala Ala Gly Ser Ala Ala Ala Ala Ala Thr Phe Gln
                20                  25                  30

Ala Thr Ser Leu Tyr Val Gly Asp Leu Asp Val Ser Val Gln Asp Ala
            35                  40                  45

Gln Leu Phe Asp Val Phe Ser Gln Val Gly Ser Val Ser Val Arg
        50                  55                  60

Val Cys Arg Asp Val Asn Thr Arg Leu Ser Leu Gly Tyr Ala Tyr Val
 65                 70                  75                  80

Asn Phe Ser Ser Pro Ala Asp Ala Ala Arg Ala Leu Glu Met Leu Asn
                85                  90                  95

Phe Thr Pro Ile Asn Gly Lys Pro Ile Arg Ile Met Tyr Ser Asn Arg
            100                 105                 110

Asp Pro Ser Ser Arg Lys Ser Gly Ala Ala Asn Ile Phe Ile Lys Asn
        115                 120                 125

Leu Asp Lys Ser Ile Asp Asn Lys Ala Leu Tyr Asp Thr Phe Ser Val
    130                 135                 140

Phe Gly Asn Ile Leu Ser Cys Lys Val Ala Thr Glu Met Ser Gly Glu
145                 150                 155                 160

Ser Lys Gly Tyr Gly Phe Val Gln Phe Glu Leu Glu Glu Ala Ala Gln
                165                 170                 175

Asn Ala Ile Ser Lys Leu Asn Gly Met Leu Leu Asn Asp Lys Lys Val
            180                 185                 190

Tyr Val Gly Pro Phe Val Arg Lys Gln Glu Arg Glu Asn Val Ser Gly
        195                 200                 205

Asn Pro Lys Phe Asn Asn Val Tyr Val Lys Asn Leu Ser Glu Ser Thr
    210                 215                 220

Thr Glu Asp Asn Leu Lys Glu Ile Phe Gly Lys Phe Gly Pro Ile Thr
225                 230                 235                 240

Ser Val Val Val Met Arg Glu Gly Asp Gly Lys Ser Arg Cys Phe Gly
                245                 250                 255
```

-continued

```
Phe Val Asn Phe Glu Asn Pro Asp Asp Ala Ala Arg Ala Val Glu Asp
                260                 265                 270
Leu Asn Gly Lys Lys Phe Asp Asp Lys Glu Trp Tyr Val Cys Arg Ala
            275                 280                 285
Gln Lys Lys Ser Glu Arg Glu Met Glu Leu Lys Glu Lys Phe Glu Lys
        290                 295                 300
Asn Ile Lys Glu Ala Ala Asp Lys Asn Gln Gly Thr Asn Leu Tyr Leu
305                 310                 315                 320
Lys Asn Leu Asp Asp Ser Ile Asp Asp Glu Lys Leu Lys Glu Ile
                325                 330                 335
Phe Ala Asp Phe Gly Thr Ile Thr Ser Cys Lys Val Met Arg Asp Leu
                340                 345                 350
Asn Gly Val Ser Lys Gly Ser Gly Phe Val Ala Phe Lys Ser Ala Glu
                355                 360                 365
Asp Ala Ser Arg Ala Leu Val Ala Met Asn Gly Lys Met Ile Gly Ser
                370                 375                 380
Lys Pro Leu Tyr Val Ala Leu Ala Gln Arg Lys Glu Glu Arg Arg Ala
385                 390                 395                 400
Arg Leu Gln Ala Gln Phe Ser Gln Met Arg Pro Met Val Met Pro Pro
                405                 410                 415
Ser Val Ala Pro Arg Met Pro Met Tyr Pro Pro Gly Val Pro Gly Val
                420                 425                 430
Gly Gln Gln Leu Phe Tyr Gly Gln Pro Pro Ala Phe Val Asn Pro
            435                 440                 445
Gln Pro Gly Phe Gly Phe Gln Gln His Leu Ile Pro Gly Met Arg Pro
        450                 455                 460
Ser Val Gly Pro Ile Pro Asn Phe Val Met Pro Met Val Gln Gln Gly
465                 470                 475                 480
Gln Gln Pro Gln Arg Pro Ala Gly Arg Arg Ala Gly Thr Gly Gly Ile
                485                 490                 495
Gln Gln Pro Met Pro Met Gly His Gln Gln Met Leu Pro Arg Gly Ser
                500                 505                 510
Arg Gly Gly Tyr Arg Tyr Ala Ser Gly Arg Gly Met Pro Asp Asn Ala
            515                 520                 525
Ser Arg Gly Val Gly Gly Leu Val Pro Ser Pro Tyr Glu Met Gly Arg
        530                 535                 540
Met Pro Leu Ser Asp Ala Gly Ala Pro Gln Val Pro Ile Gly Ala
545                 550                 555                 560
Leu Ala Ser Ala Leu Ala Asn Ser Pro Pro Asp Gln Arg Leu Met
                565                 570                 575
Leu Gly Glu Ser Leu Tyr Pro Leu Val Asp Gln Leu Glu His Asp Gln
                580                 585                 590
Ala Ala Lys Val Thr Gly Met Leu Glu Met Asp Gln Thr Glu Val
                595                 600                 605
Leu His Leu Ile Glu Ser Pro Asp Ala Leu Lys Ala Lys Val Ala Glu
        610                 615                 620
Ala Met Glu Val Leu Arg Asn Ala Gln Gln Gln Ala Asn Thr Pro
625                 630                 635                 640
Thr Asp Gln Leu Ala Ala Leu Thr Leu Ser Asp Gly Val Val Ser
                645                 650                 655

<210> SEQ ID NO 5
<211> LENGTH: 527
```

```
<212> TYPE: DNA
<213> ORGANISM: Glycine max
<220> FEATURE:
<221> NAME/KEY: unsure
<222> LOCATION: (480)

<400> SEQUENCE: 5
cggatgaaga gttgatgaaa ttttttggag aatatggtac cattactagt gctgtaataa      60
tgagggacgc agacggtaaa tcaaggtgtt ttggctttgt caattttgaa acccagatg     120
atgctgccaa agctgttgaa ggacttaatg ggaagaaagt tgatgataag gagtggtatg     180
ttggaaaagc ccagaaaaaa tctgagcgtg aacaagaact gaaaggacgg tttgagcaga     240
gtataaagga atctgctgac aaatatcaag gtgtgaacct gtatctcaag aacttggatg     300
atactatcag tgatgaaaaa cttaaggaaa tgtttgctga atatggtaca ataacttcat     360
gcaaggttat gcgagacccc actggaatcg gtagaggatc aggatttgtt gcattttcaa     420
ctcctgagga agcatctcgt gctctcggtg agatgaatgg taaaatgatt gctggaaaan     480
ctcctgtacg ttgccccttg cacaagaaga aagaagaca gaagagc                   527

<210> SEQ ID NO 6
<211> LENGTH: 428
<212> TYPE: PRT
<213> ORGANISM: Glycine max

<400> SEQUENCE: 6

Asp Glu Glu Leu Met Lys Phe Gly Glu Tyr Gly Thr Ile Thr Ser
  1               5                  10                  15

Ala Val Ile Met Arg Asp Ala Asp Gly Lys Ser Arg Cys Phe Gly Phe
                 20                  25                  30

Val Asn Phe Glu Asn Pro Asp Asp Ala Ala Lys Ala Val Glu Gly Leu
             35                  40                  45

Asn Gly Lys Lys Val Asp Asp Lys Glu Trp Tyr Val Gly Lys Ala Gln
         50                  55                  60

Lys Lys Ser Glu Arg Glu Gln Glu Leu Lys Gly Arg Phe Glu Gln Ser
 65                  70                  75                  80

Ile Lys Glu Ser Ala Asp Lys Tyr Gln Gly Val Asn Leu Tyr Leu Lys
                 85                  90                  95

Asn Leu Asp Asp Thr Ile Ser Asp Glu Lys Leu Lys Glu Met Phe Ala
            100                 105                 110

Glu Tyr Gly Thr Ile Thr Ser Cys Lys Val Met Arg Asp Pro Thr Gly
        115                 120                 125

Ile Gly Arg Gly Ser Gly Phe Val Ala Phe Ser Thr Pro Glu Glu Ala
    130                 135                 140

Ser Arg Ala Leu Gly Glu Met Asn Gly Lys Met Ile Ala Gly Lys Pro
145                 150                 155                 160

Leu Tyr Val Ala Leu Ala Gln Arg Lys Glu Asp Arg Arg Ala Arg Leu
                165                 170                 175

Gln Ala Gln Phe Ser Gln Met Arg Pro Val Ala Ile Thr Pro Ser Val
            180                 185                 190

Ala Pro Arg Met Pro Leu Tyr Pro Pro Gly Ala Pro Gly Leu Gly Gln
        195                 200                 205

Gln Phe Leu Tyr Gly Gln Gly Pro Ala Met Met Pro Pro Gln Ala
    210                 215                 220

Gly Phe Gly Tyr Gln Gln Gln Leu Val Pro Gly Met Arg Pro Gly Gly
225                 230                 235                 240
```

Gly Pro Met Pro Ser Phe Phe Val Pro Met Val Gln Gln Gly Gln Gln
                245                 250                 255

Gly Gln Arg Pro Gly Gly Arg Arg Gly Thr Gly Pro Val Gln Gln Pro
            260                 265                 270

Gln Gln Pro Met Pro Met Met Gln Gln Gln Met Leu Pro Arg Gly Arg
        275                 280                 285

Val Tyr Arg Tyr Pro Pro Gly Arg Asn Met Gln Asp Val Pro Leu Gln
        290                 295                 300

Gly Val Ala Gly Gly Met Met Ser Val Pro Tyr Asp Met Gly Gly Leu
305                 310                 315                 320

Pro Ile Arg Asp Ala Val Gly Gln Pro Met Pro Ile Gln Ala Leu Ala
                325                 330                 335

Thr Ala Leu Ala Asn Ala Pro Pro Glu Gln Arg Thr Met Leu Gly
            340                 345                 350

Glu Ala Leu Tyr Pro Leu Val Asp Gln Leu Glu His Asp Ala Ala Ala
            355                 360                 365

Lys Val Thr Gly Met Leu Leu Glu Met Asp Gln Pro Glu Val Leu His
        370                 375                 380

Leu Ile Glu Ser Pro Asp Ala Leu Lys Ala Lys Val Ala Glu Ala Met
385                 390                 395                 400

Asp Val Leu Arg Asn Val Ala Gln Gln Gln Thr Asn Pro Ala Asp Gln
                405                 410                 415

Leu Ala Ser Leu Ser Leu Asn Asp Asn Leu Val Ser
                420                 425

<210> SEQ ID NO 7
<211> LENGTH: 386
<212> TYPE: DNA
<213> ORGANISM: Zea mays
<220> FEATURE:
<221> NAME/KEY: unsure
<222> LOCATION: (12)..(13)

<400> SEQUENCE: 7
ggaaatcatg annatcctga tgaggagaac attgaagcat tatgcaaatt gatgagtaca      60
attggtgata tgattgatca tgtaaaggca aaggagcaca tggatgccta ttttagtatg     120
atgcagataa tgtcaacaaa tcagaagttg tcttctcgtg taaggtttat gttgagagat     180
tcaatcgacc tgaggagaaa taaatggcag caaaggcgta aagtcgaagg tcccaagaag     240
attgaggagg ttcacagaga tgcagcacaa gaaagacatg cccagtcgag taggttggga     300
cgtggtccag ctgttagttc tgttccaaga agagcacatc ctatggatta tggccctcgt     360
ggaccatctg catcagcatc ctcaag                                          386

<210> SEQ ID NO 8
<211> LENGTH: 417
<212> TYPE: PRT
<213> ORGANISM: Zea mays

<400> SEQUENCE: 8

Asp Glu Glu Asn Ile Glu Ala Leu Cys Lys Leu Met Ser Thr Ile Gly
  1               5                  10                  15

Asp Met Ile Asp His Val Lys Ala Lys Glu His Met Asp Ala Tyr Phe
                20                  25                  30

Ser Met Met Gln Ile Met Ser Thr Asn Gln Lys Leu Ser Ser Arg Val
            35                  40                  45

Arg Phe Met Leu Arg Asp Ser Ile Asp Leu Arg Arg Asn Lys Trp Gln

|     |     |     |     | 50  |     |     |     |     | 55  |     |     |     |     | 60  |     |
| --- | --- | --- | --- | --- | --- | --- | --- | --- | --- | --- | --- | --- | --- | --- | --- |

Gln Arg Arg Lys Val Glu Gly Pro Lys Lys Ile Glu Glu Val His Arg
65                  70                  75                  80

Asp Ala Ala Gln Glu Arg His Ala Gln Ser Ser Arg Leu Gly Arg Gly
            85                  90                  95

Pro Ala Val Ser Ser Val Pro Arg Arg Ala His Pro Met Asp Tyr Gly
            100                 105                 110

Pro Arg Gly Pro Ser Ala Ser Ala Ser Ser Ser Gln Gln Gly Ser
        115                 120                 125

Ile Arg Gly Met Pro Pro His Ser Arg Gly Ser Gln Asp Ile Arg His
        130                 135                 140

Asp Glu Arg His Gln Phe Asp Asn Arg Thr Val Leu Pro Gln Arg Val
145                 150                 155                 160

Val Lys Asp Glu Ala Ile Thr Leu Gly Pro Gln Gly Gly Leu Ala Arg
                165                 170                 175

Gly Met Ser Ile Arg Gly Gln Pro Val Ser Asn Thr Glu Ile Pro
            180                 185                 190

Ser Val Ile Asp His Arg Arg Ile Val Ser Ser Asn Gly Tyr Asn
        195                 200                 205

Ser Ala Ala Asp Trp Thr Ser Ser Gly Arg Glu Asp Ser Asn Ser
210                 215                 220

Arg Leu Pro Asp Arg Thr Ser Gly Arg Ile Pro Ala Ser Ser Gln Ser
225                 230                 235                 240

Ala Val Thr Ser Gln Arg Pro Ala Ser Gln Glu Gly Arg Ser Arg Ser
                245                 250                 255

Lys Ser Tyr Ser Glu Asp Glu Leu Arg Glu Lys Ser Val Leu Thr Ile
            260                 265                 270

Arg Glu Tyr Tyr Ser Ala Lys Asp Glu Lys Glu Val Val Leu Cys Ile
        275                 280                 285

Glu Glu Leu Asn Ala Pro Asn Phe Tyr Pro Phe Leu Val Ser Leu Trp
        290                 295                 300

Val Asn Asp Ser Phe Glu Arg Lys Asp Met Glu Arg Glu Leu Leu Ala
305                 310                 315                 320

Lys Leu Leu Val Ser Leu Cys Ser Gly Arg His Asn Leu Leu Ser Lys
                325                 330                 335

Gln Gln Leu Ser Asp Gly Leu Ser Asn Val Leu Ala Ser Leu Glu Asp
            340                 345                 350

Asn Leu Ser Asp Ala Pro Arg Ala Thr Glu Tyr Leu Gly Arg Leu Leu
        355                 360                 365

Ala Arg Phe Val Glu Glu Ser Ile Leu Leu Gln Glu Val Gly Lys
        370                 375                 380

Leu Ile Gln Glu Ser Gly Glu Glu Pro Gly Tyr Leu Ile Gln Gly Gly
385                 390                 395                 400

Ile Ala Ala Asp Ile Leu Gly Ala Val Leu Asp Ser Ile Lys Ser Asp
                405                 410                 415

Lys

```
<210> SEQ ID NO 9
<211> LENGTH: 609
<212> TYPE: DNA
<213> ORGANISM: Glycine max
<220> FEATURE:
<221> NAME/KEY: unsure
<222> LOCATION: (484)
<220> FEATURE:
```

<221> NAME/KEY: unsure
<222> LOCATION: (487)
<220> FEATURE:
<221> NAME/KEY: unsure
<222> LOCATION: (523)
<220> FEATURE:
<221> NAME/KEY: unsure
<222> LOCATION: (556)
<220> FEATURE:
<221> NAME/KEY: unsure
<222> LOCATION: (558)
<220> FEATURE:
<221> NAME/KEY: unsure
<222> LOCATION: (565)
<220> FEATURE:
<221> NAME/KEY: unsure
<222> LOCATION: (578)
<220> FEATURE:
<221> NAME/KEY: unsure
<222> LOCATION: (589)
<220> FEATURE:
<221> NAME/KEY: unsure
<222> LOCATION: (591)
<220> FEATURE:
<221> NAME/KEY: unsure
<222> LOCATION: (595)
<220> FEATURE:
<221> NAME/KEY: unsure
<222> LOCATION: (603)
<220> FEATURE:
<221> NAME/KEY: unsure
<222> LOCATION: (607)

<400> SEQUENCE: 9

```
gcaatccacg cagtccaccc atctgagcat taggagataa cattgatgat cctcttggac      60
caaaatccat agggattctt cgaggtggat tgttgcctgg accacgaccc agcctactag     120
cttgggccag cctctcttga gaagcatctc tgtgcacctc ctcaatcttc ttcggacctt     180
caacctttct tctttgttgc catttattct ttctcaaatc aatgacatcc ttcaacatga     240
acctcaacct agaagataaa ttcatgttgt tgataatga tctcatcatt tcaaaatatg      300
catccatatg ttccttgggc tttgggatgg caatcatctc cccaatagta ctcatcagct     360
tgcacaaagc ttcaatatct cctcatccgg tcctgatact gacccaataa cttcttgatg     420
catcatgcat tacctttcgt aacatttctt cttaatagtt ctcaatcaat ctgatatccc     480
caanaangtc tctgcttggt cgtttcctcc cttcccatta ganagttgac tcacccatag     540
cttatacttc tctgcncntt ccccnccaaa tttccggnat tttaaaaanc ntaangtact     600 tangctncg                                                             609
```

<210> SEQ ID NO 10
<211> LENGTH: 147
<212> TYPE: PRT
<213> ORGANISM: Glycine max
<220> FEATURE:
<221> NAME/KEY: UNSURE
<222> LOCATION: (10)..(11)

<400> SEQUENCE: 10

```
Glu Gly Arg Lys Arg Pro Ser Arg Asp Xaa Xaa Gly Asp Ile Arg Leu
 1               5                  10                  15

Ile Glu Asn Tyr Glu Glu Met Leu Arg Lys Val Met His Asp Ala Ser
            20                  25                  30

Arg Ser Tyr Trp Val Ser Ile Arg Thr Gly Gly Asp Ile Glu Ala Leu
        35                  40                  45

Cys Lys Leu Met Ser Thr Ile Gly Glu Met Ile Ala Ile Pro Lys Pro
    50                  55                  60
```

Lys Glu His Met Asp Ala Tyr Phe Glu Met Met Arg Ser Leu Ser Asn
 65                  70                  75                  80

Asn Met Asn Leu Ser Ser Arg Leu Arg Phe Met Leu Lys Asp Val Ile
             85                  90                  95

Asp Leu Arg Lys Asn Lys Trp Gln Gln Arg Arg Lys Val Glu Gly Pro
            100                 105                 110

Lys Lys Ile Glu Glu Val His Arg Asp Ala Ser Gln Glu Arg Leu Ala
        115                 120                 125

Gln Ala Ser Arg Leu Gly Arg Gly Pro Gly Asn Pro Pro Arg Arg
    130                 135                 140

Ile Pro Met
145

<210> SEQ ID NO 11
<211> LENGTH: 442
<212> TYPE: PRT
<213> ORGANISM: Triticum aestivum

<400> SEQUENCE: 11

Met Ala Ala Ala Ala Ser Ser Ala Ser Gly Gly Ser Ala Ala Ala Ala
  1               5                  10                  15

Ala Ala Ala Ala Ala Ala Ser Ser Ala Thr Ser Tyr Val Gly Asp
             20                  25                  30

Asp Val Ser Val Asp Ala Asp Val Ala Gly Gly Val Val Ser Val Arg
         35                  40                  45

Val Cys Arg Asp Val Thr Ser Arg Lys Ser Gly Tyr Ala Tyr Val Asn
     50                  55                  60

Tyr Asn Thr Ala Asp Ala Ala Arg Ala Met Asn Thr Asn Gly Arg Arg
 65                  70                  75                  80

Met Tyr Ser Asn Arg Asp Ser Arg Lys Ser Gly Thr Ala Asn Lys Asn
             85                  90                  95

Asp Lys Ser Asp Asn Lys Ala Tyr Asp Thr Cys Val Gly Asn Ser Cys
            100                 105                 110

Lys Val Ala Thr Asp Ala Gly Ser Lys Gly Tyr Gly Val Tyr Arg Asp
        115                 120                 125

Ala Ala His Ala Ala Lys Asn Gly Met Met Asn Asp Lys Lys Val Tyr
    130                 135                 140

Val Gly Val Arg Lys Arg Asp Asn Ser Gly Asn Val Lys Asn Asn Val
145                 150                 155                 160

Tyr Val Lys Asn Ala Thr Thr Thr Asp Asp Lys Gly Lys Gly Ala Thr
                165                 170                 175

Ser Val Val Val Met Arg Asp Gly Asp Gly Arg Ser Lys Cys Gly Val
                180                 185                 190

Asn Ser Asp Ala Ala Val Asp Asn Gly Lys Lys Ser Asp Lys Trp
            195                 200                 205

Tyr Val Gly Arg Ala Lys Lys Ser Arg Lys Lys Asn Ala Ala Asp
        210                 215                 220

Lys Tyr Asn Thr Asn Tyr Lys Asn Asp Thr Val Asp Asp Lys Arg
225                 230                 235                 240

Ala Gly Thr Thr Ser Cys Lys Val Met Arg Asp Ser Asn Gly Ala Ser
                245                 250                 255

Arg Gly Ser Gly Val Ala Lys Ser Ala Asp Asp Ala Ser Arg Ala Ala
            260                 265                 270

Met Asn Asn Lys Met Val Gly Asn Lys Tyr Val Ala Ala Arg Lys Asp

-continued

```
              275                 280                 285
Arg Lys Ala Arg Ala Ser Met Arg Val Met Ala Thr Val Gly Arg Met
    290                 295                 300
Met Gly Val Val Gly Met Tyr Gly Ala Asn Gly Gly Met Gly Met Arg
305                 310                 315                 320
Gly Gly Ala Met Asn Met Met Met Val Gly Arg Ala Gly Arg Arg Ala
                325                 330                 335
Gly Ala Gly Gly Met Ser Met Met Gly Met Gly Arg Gly Gly Gly Arg
                340                 345                 350
Gly Tyr Arg Tyr Thr Gly Arg Gly Met Asp Ala Met His Gly Val Gly
            355                 360                 365
Gly Val Met Thr Ser Tyr Met Gly Gly Met Met Arg Asp Ala Gly Ser
        370                 375                 380
Val Gly Ala Ala Ser Ala Ala Asn Ser Thr Arg Met Met Gly Asn Tyr
385                 390                 395                 400
Val Asp His Asp Ala Ala Lys Val Thr Gly Met Met Asp Thr Val His
                405                 410                 415
Ser Asp Ala Lys Ala Lys Val Ala Ala Met Val Arg Ser Ala His Thr
            420                 425                 430
Asn Ser Ala Ser Ser Asn Asp Gly Ser Ser
            435                 440
```

FACTORS INVOLVED IN GENE EXPRESSION

This application claims the benefit of U.S. Provisional Application No. 60/092,415, filed Jul. 10, 1998.

FIELD OF THE INVENTION

This invention is in the field of plant molecular biology. More specifically, this invention pertains to nucleic acid fragments encoding factors involved in gene expression in plants and seeds.

BACKGROUND OF THE INVENTION

Binding of 40S ribosomal subunit to mRNA requires several initiation factors, including proteins that recognize the cap structure. In the initiation of translation in eukaryotes, binding of the small ribosomal subunit to the mRNA results from recognition of the 5' cap structure of the mRNA by the cap-binding complex eukaryotic initiation factor 4F (eIF4F). This factor is itself a three-subunit complex comprising the cap binding protein eIF4E, eIF4A, an ATP-dependent RNA helicase, and eIF-4 gamma, which interacts with both eIF4E and eIF4A and enhances cap binding by eIF4E. Eukaryotic protein synthesis initiation factor eIF-4 gamma, also known as p220, is involved in the recognition of the mRNA cap, ATP-dependent unwinding of 5'-terminal secondary structure and recruitment of mRNA to the ribosome.

Infection of mammalian cells by picornaviruses results in the proteolytic cleavage of eIF-4 gamma, severely restricting cap-dependent translation initiation but permitting cap-independent initiation to proceed from an internal ribosome entry site. Processing of eIF-4 gamma by potyviruses (plant members of the picornavirus superfamily) has not been shown to date but this process may also occur in plants.

eIF4F activity is impaired during heat shock, when binding of eIF4E to its inhibitory protein (4E-BP1) is increased and the amount of eIF-4 gamma is decreased. Heat shock protein mRNAs are believed to be relatively cap-independent, providing a mechanism for the selective up-regulation of the synthesis of heat shock proteins and other stress proteins during heat shock (Vries et al. (1997) *J. Biol. Chem.* 272: 32779–32784). The eIF-4 gamma polypeptide from rabbit or human is 154 kDa (1,396 amino acid residues) and contains sequence motifs of potential interest: a sequence (AGLGPR) that is similar to the substrate recognition sequence of protease 2A from rhinovirus serotype 14, five PEST regions with scores greater than 10 (which are characteristic of rapidly degraded proteins), stretches of polyglutamic acid, and numerous potential phosphorylation sites (Rychlik et al. (1992) *J. Biol. Chem.* 267: 23226–23231). Sequences encoding eIF-4 gamma have been studied in humans, mammals, and yeast.

The mRNA 3' poly(A) tail and the associated poly(A)-binding protein also regulate translational initiation, probably by interacting with the 5' end of the mRNA (Craig et al. (1998) *Nature* 392:520–523). The poly(A) binding protein is essential for viability of the yeast *Saccharomyces cerevisiae*. The amino acid sequence of the protein indicates that it consists of four ribonucleoprotein consensus sequence-containing RNA-binding domains and a proline-rich auxiliary domain at the carboxyl terminus. Specific poly(A) binding activity was found only in the two amino-terminal RNA-binding domains which, interestingly, are dispensable for viability of yeast cells (Burd et al. (1991) *Mol. Cell Biol.* 11: 3419–3424). Multiple poly(A) binding protein-related sequences have been cloned from *Arabidopsis thaliana* suggesting that this protein is encoded by a multigene family.

SUMMARY OF THE INVENTION

The instant invention relates to isolated nucleic acid fragments encoding factors involved in gene expression. Specifically, this invention concerns an isolated nucleic acid fragment encoding a poly(A) binding protein or a eukaryotic translation initiation factor-4 gamma (eIF-4 gamma) and an isolated nucleic acid fragment that is substantially similar to an isolated nucleic acid fragment encoding a poly(A) binding protein or a eIF-4 gamma. In addition, this invention relates to a nucleic acid fragment that is complementary to the nucleic acid fragment encoding poly(A) binding protein or eIF-4 gamma.

An additional embodiment of the instant invention pertains to a polypeptide encoding all or a substantial portion of a factor involved in gene expression selected from the group consisting of poly(A) binding protein and eIF-4 gamma.

In another embodiment, the instant invention relates to a chimeric gene encoding a poly(A) binding protein or a eIF-4 gamma, or to a chimeric gene that comprises a nucleic acid fragment that is complementary to a nucleic acid fragment encoding a poly(A) binding protein or a eIF-4 gamma, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a poly(A) binding protein or a eIF-4 gamma, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a poly(A) binding protein or a eIF-4 gamma in a transformed host cell comprising: a) transforming a host cell with a chimeric gene comprising a nucleic acid fragment encoding a poly(A) binding protein or a eIF-4 gamma; and b) growing the transformed host cell under conditions that are suitable for expression of the chimeric gene wherein expression of the chimeric gene results in production of altered levels of poly(A) binding protein or eIF-4 gamma in the transformed host cell.

An additional embodiment of the instant invention concerns a method for obtaining a nucleic acid fragment encoding all or a substantial portion of an amino acid sequence encoding a poly(A) binding protein or a eIF-4 gamma.

A further embodiment of the instant invention is a method for evaluating at least one compound for its ability to inhibit the activity of a poly(A) binding protein or a eIF-4 gamma, the method comprising the steps of: (a) transforming a host cell with a chimeric gene comprising a nucleic acid fragment encoding a poly(A) binding protein or a eIF-4 gamma, operably linked to suitable regulatory sequences; (b) growing the transformed host cell under conditions that are suitable for expression of the chimeric gene wherein expression of the chimeric gene results in production of poly(A)

binding protein or eIF-4 gamma in the transformed host cell; (c) optionally purifying the poly(A) binding protein or the eIF-4 gamma expressed by the transformed host cell; (d) treating the poly(A) binding protein or the eIF-4 gamma with a compound to be tested; and (e) comparing the activity of the poly(A) binding protein or the eIF-4 gamma that has been treated with a test compound to the activity of an untreated poly(A) binding protein or eIF-4 gamma, thereby selecting compounds with potential for inhibitory activity.

BRIEF DESCRIPTION OF THE DRAWING AND SEQUENCE DESCRIPTIONS

The invention can be more fully understood from the following detailed description and the accompanying drawing and Sequence Listing which form a part of this application.

FIG. 1 depicts the amino acid sequence alignment between the poly (A) binding protein from *Triticum aestivum* (NCBI General Identifier No. 1737492; SEQ ID NO:11), the instant corn clone p0083.cldcq55r (SEQ ID NO:2), the instant rice clone rsr9n.pk005.117 (SEQ ID NO:4) and the instant soybean clone sdp2c.pk003.112 (SEQ ID NO:6). The top row indicates with asterisks (*) the amino acids conserved among all sequences. 1-1 positions 1 through 240; 1-2 sitions 241 through 480; 1-3 positions 481 through 662.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Factors Involved in Gene Expression

| Protein | Clone Designation | SEQ ID NO: (Nucleotide) | (Amino Acid) |
|---|---|---|---|
| Corn Poly (A) binding protein | p0083.cldcq55r | 1 | 2 |
| Rice Poly (A) binding protein | rsr9n.pk005.117 | 3 | 4 |
| Soybean Poly (A) binding protein | sdp2c.pk003.112 | 5 | 6 |
| Corn eIF-4 gamma | p0079.ctxmf11r | 7 | 8 |
| Soybean eIF-4 gamma | sr1.pk0162.e10 | 9 | 10 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent identity of the amino acid sequences that they encode to the amino acid sequences disclosed herein, as determined by algorithms commonly employed by those skilled in this art.

Preferred are those nucleic acid fragments whose nucleotide sequences encode amino acid sequences that are 80% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms. "Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several factors involved in gene expression have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other poly(A) binding proteins or eIF-4 gammas, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of RNA stability and/or protein expression in those cells. Poly(A) binding protein and eIF-4 gamma are involved in the control of mRNA translation and stability. Modifying one or both of these factors may result in changes in the stability of the RNA and differences in translation efficiency. Thus, these factors may be used as targets for herbicides. Because in mammals eIF-4 gamma is proteolytically processed by picornaviruses, it may be useful to overexpress this factor in plants in order to avoid the interruption of cap-dependent translation. Underexpression of this factor, on the other hand may result in plants which are more resistant to heat shock.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *MoL Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) Plant Phys.100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded factor involved in gene expression. An example of a vector for high level expression of the instant polypeptides in a bacterial host is provided (Example 8).

Additionally, the instant polypeptides can be used as a targets to facilitate design and/or identification of inhibitors of those enzymes that may be useful as herbicides. This is desirable because the polypeptides described herein catalyze various steps in mRNA translation and stability. Accordingly, inhibition of the activity of one or more of the enzymes described herein could lead to inhibition plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bematzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 1 7:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad Sci USA* 86:9402; Koes et al. (1995) *Proc. Natl. Acad Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice and soybean tissues were prepared. The characteristics of the libraries are described below.

TABLE 2 cDNA Libraries from Corn, Rice and Soybean

| Library | Tissue | Clone |
|---|---|---|
| p0079 | Corn (Cross of Tuxpeno and Opaque 2) Whole Kernels, 18 Days After Pollination* | p0079.ctxmf11r |
| p0083 | Corn Whole Kernels 7 Days After Pollination | p0083.cldcq55r |
| rsr9n | Rice Leaf 15 Days After Germination Harvested 2–72 Hours Following Infection With *Magnaporta grisea* (4360-R-62 and 4360-R-67)* | rsr9n.pk005.117 |
| sdp2c | Soybean Developing Pods (6–7 mm) | sdp2c.pk003.112 |
| sr1 | Soybean Root | sr1.pk0162.e10 |

*These libraries were normalized essentially as described in U.S. Pat. No. 5,482,845, incorporated herein by reference.

CDNA libraries may be prepared by any one of many methods available. For example, the cDNAs may be introduced into plasmid vectors by first preparing the cDNA libraries in Uni-ZAP* XR vectors according to the manufacturer's protocol (Stratagene Cloning Systems, La Jolla, Calif.). The Uni-ZAP* XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding factors involved in gene expression were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Poly (A) Binding Protein

The BLASTX search using the EST sequences from clones listed in Table 3 revealed similarity of the polypeptides encoded by the cDNAs to Poly (A) binding protein from *Triticum aestivum* (NCBI General Identifier No. 1737492). Shown in Table 3 are the BLAST results for the sequences of the entire cDNA inserts comprising the indicated cDNA clones ("FIS"):

TABLE 3

BLAST Results for Sequences Encoding Polypeptides Homologous to Poly (A) Binding Protein

| Clone | Status | BLAST pLog Score 1737492 |
|---|---|---|
| p0083.cldcq55r | FIS | 254.0 |
| rsr9n.pk005.117 | FIS | 254.0 |
| sdp2c.pk003.112 | FIS | 167.0 |

The nucleotide sequence from ccase-b.pkOO21.a10 is included in the p0083.cldcq55r FIS. The nucleotide sequence from rls48.pkb0001.b2 is included in the rsr9n.pk005.117 FIS. The nucleotide sequence from the contig assembled from se 1.19d04, se1.pk0015.d6, ses8w.pk0035.f7 and sf1.pk0097.b12 is included in the sdp2c.pk003.112 FIS.

FIG. 1 presents an alignment of the amino acid sequences set forth in SEQ ID NOs:2, 4 and 6 and the *Triticum aestivum* sequence (SEQ ID NO:11). The data in Table 4 represents a calculation of the percent identity of the amino acid sequences set forth in SEQ ID NOs:2, 4 and 6 and the *Triticum aestivum* sequence (SEQ ID NO:11).

TABLE 4

Percent Identity of Amino Acid Sequences Deduced From the Nucleotide Sequences of cDNA Clones Encoding Polypeptides Homologous to Poly (A) Binding Protein

| SEQ ID NO. | Percent Identity to 1737492 |
|---|---|
| 2 | 14.9 |
| 4 | 19.9 |
| 6 | 11.2 |

Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode an entire corn, an entire rice and a substantial portion of a soybean poly (A) binding protein. These sequences represent the first corn and soybean sequences encoding poly(A) binding protein, and a heretofore unknown rice poly(A) binding protein.

Example 4

Characterization of cDNA Clones Encoding

Eukaryotic Translation Initiation Factor-4 Gamma (eIF-4 gamma)

The BLASTX search using the EST sequences from clones listed in Table 4 revealed similarity of the polypeptides encoded by the cDNAs to eIF-4 gamma from human and rabbit (NCBI General Identifier Nos. 3941724 and 729820, respectively). Shown in Table 5 are the BLAST results for individual ESTs:

TABLE 5

BLAST Results for Sequences Encoding Polypeptides Homologous to eIF-4 gamma

| Clone | Status | BLAST pLog Score | |
|---|---|---|---|
| | | 3941724 | 729820 |
| p0079.ctxmf11r | EST | 34.40 | 33.10 |
| sr1.pk0162.e10 | EST | 15.15 | 16.00 |

The data in Table 6 represents a calculation of the percent identity of the amino acid sequences set forth in SEQ ID NOs:8 and 10 and the human and rabbit sequences.

TABLE 6

Percent Identity of Amino Acid Sequences Deduced From the Nucleotide Sequences of cDNA Clones Encoding Polypeptides Homologous to eIF-4 gamma

| | Percent Identity to | |
|---|---|---|
| SEQ ID NO. | 3941724 | 729820 |
| 8 | 25.2 | 25.7 |
| 10 | 29.9 | 28.6 |

Sequence alignments and percent identity calculations were performed using the Megalign program of the LASAR-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Sequence alignments and BLAST scores and probabilities indicate that the nucleic acid fragments comprising the instant cDNA clones encode a substantial portion of a corn and a portion of a soybean eIF-4 gamma. These sequences represent the first plant sequences encoding eIF-4 gamma.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega).

Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and the 3' region of the nopaline synthase gene from the T-DNA of the Ti plasmid of Agrobacterium tumefaciens.

The particle bombardment method (Klein et al. (1987) Nature 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuiged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 7

Expression of Chimeric Genes in Dicot Cells

A seed-specific expression cassette composed of the promoter and transcription terminator from the gene encoding the β subunit of the seed storage protein phaseolin from the bean Phaseolus vulgaris (Doyle et al. (1986) J. Biol. Chem. 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) Nature (London) 327:70, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) Nature 313:810–812), the hygromycin phosphotransferase gene from plasmid pJR225 (from E. coli; Gritz et al.(1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order):5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 μg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 9

Evaluating Compounds for Their Ability to Inhibit the Activity of Factor Involved in Gene Expression The polypeptides described herein may be produced using any number of methods known to those skilled in the art. Such methods include, but are not limited to, expression in bacteria as described in Example 8, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for poly (A) binding protein are presented by Berger et al. (1992) *Biochem. Cell Biol.* 70:770–778. Assays for eIF-4 gamma are presented by Morley (1993) *Eur J Biochem* 218:39–48.

What is claimed is:

1. An isolated polynucleotide encoding a polyadenylated RNA-binding protein having an amino acid sequence identity that is at least 82% identical to the amino acid sequence set forth in a member selected from the group consisting of SEQ ID NO:2, SEQ ID NO:4, and SEQ ID NO:6.

2. The isolated polynucleotide of claim 1 wherein said polynucleotide is RNA.

3. The isolated nucleic acid fragment of claim 1 wherein the nucleotide sequence of the fragment comprises the sequence set forth in a member selected from the group consisting of SEQ ID NO:1, SEQ ID NO:3 and SEQ ID NO:5.

4. A chimeric gene comprising the polynucleotide of claim 1 operably linked to at least one regulatory sequence.

5. A transformed host cell comprising the chimeric gene of claim 4.

6. An isolated complement of the polynucleotide of claim 1, wherein (a) the complement and the polynucleotide consist of the same number of nucleotides, and (b) the nucleotide sequences of the complement and the polynucleotide have 100% complementarity.

7. The isolated polynucleotide of claim 1, wherein the amino acid sequence identity is at least 90%.

8. The isolated polynucleotide of claim 1, wherein the amino acid sequence identity is at least 95%.

9. The isolated polynucleotide of claim 1, wherein the polyadenylated RNA-binding protein has an amino acid sequence selected from the group consisting of SEQ ID NO:2, SEQ ID NO:4, and SEQ ID NO:6.

* * * * *